United States Patent [19]
Whaley

[11] Patent Number: 5,995,938
[45] Date of Patent: Nov. 30, 1999

[54] MEDICATION COMPLIANCE SYSTEM

[76] Inventor: Susan S. Whaley, 1022 E. 28th Ave., Spokane, Wash. 99203

[21] Appl. No.: 08/803,862

[22] Filed: Feb. 24, 1997

Related U.S. Application Data

[60] Provisional application No. 60/012,715, Feb. 27, 1996.

[51] Int. Cl.$^6$ .................................................. G06F 159/00
[52] U.S. Cl. ........................................................... 705/3
[58] Field of Search ........................... 705/1–4; 283/81, 283/112, 113; 215/230

[56] References Cited

U.S. PATENT DOCUMENTS

| | | | |
|---|---|---|---|
| 4,208,983 | 6/1980 | Buckley | 116/205 |
| 4,962,491 | 10/1990 | Schaefer | 368/21 |
| 5,011,032 | 4/1991 | Rollman | 215/230 |
| 5,102,169 | 4/1992 | Mayfield | 283/115 |
| 5,193,855 | 3/1993 | Shamos | 283/117 |
| 5,299,701 | 4/1994 | Barker et al. | 215/230 |
| 5,502,944 | 4/1996 | Kraft et al. | 53/55 |

*Primary Examiner*—Frantzy Poinvil
*Attorney, Agent, or Firm*—Wells, St. John, Roberts, Gregory & Matkin P.S.

[57] ABSTRACT

A medication compliance system having an output device; and a computer in communication with the output device and having loaded therein a computer program to define a particular logic circuit which generates a graphical user interface with which a user indicates the number of times a particular pharmaceutical is to be taken during a day, and which causes the output device to print a label having data thereon identifying the pharmaceutical, and having a shape thereon representing the number of times a day, or the particular time of day the pharmaceutical is to be taken.

22 Claims, 9 Drawing Sheets

| MEDICINES | MORNING | NOON | EVENING | BEDTIME | SPECIAL |
|---|---|---|---|---|---|
| SULFASALAZINE 500mg | ⧖ ⧖ | | ⧖ ⧖ | | |
| QUERCETIN 50mg | B4 MEALS | B4 MEALS | B4 MEALS | | |
| JUICY FRUIT C | ▨ | ▨ | ▨ | ▨ | |
| ZOLOFT 100mg | | | | 187 ☾ | |
| | | | | | |
| | | | | | |
| | | | | | |
| | | | | | |

FIG. 1

| MEDICINES | MORNING | NOON | EVENING | BEDTIME | SPECIAL |
|---|---|---|---|---|---|
| CAL APATITE 100mg | ▲ | ▲ | ▲ | | |
| PYCNOGENOLS 25mg | ⋈ | | ⋈ | | |
| ANTI-OXIDANT | BETWEEN MEALS | | ▲ | | |
| PERIDONTAL COMPLEX | BETWEEN MEALS | ○ | ▲ | | |
| VIT C 1000mg | ▲▲ | ▲▲ | | | |
| ISOCORT | | ▲▲ | ▲▲ | | |

MEDICATION COMPLIANCE SYSTEM

PRIOR PROVISIONAL APPLICATION

This application claims priority of U.S. Provisional application Ser. No. 60/012,715, filed Feb. 27, 1996.

COPYRIGHT AUTHORIZATION

A portion of the disclosure of this prior patent application contains material which is subject to copyright protection. The owner has no objection to the facsimile reproduction by anyone of the patent application document or the patent disclosure, as it appears in the patent and Trademark Office patent file or records, but otherwise reserves all copyright rights whatsoever.

TECHNICAL FIELD

The invention relates to systems that produce visual aids. More particularly, the invention relates to systems that produce visual aids for pharmaceutical applications.

BACKGROUND OF THE INVENTION

With advancements in medicine and the development of high powered drugs, people are living longer. A major problem confronted by the chronically ill and the elderly, is the successful management of multiple medications. Errors in the time of medication, as well as the number of medications taken is a serious health care issue. Forty percent of people in hospitals are admitted due to drug contraindications. This statistic contributes to both increased health care costs, and to the lowered effectiveness of drugs.

Despite pharmaceutical refinements making fewer drugs necessary on a daily basis for the duration of treatment, the multiple number of medications can be confusing and problematic for patients. Multiple medications may also cause various visual impairments in some patients that hinder interpretation of the instructions provided.

"Homemade" systems become cumbersome and difficult to edit when there are changes or modifications in treatment. Plastic box dispensers are also limiting. They do not accommodate a large number of medications (and require they be in pill form in order to fit into the compartments) and they do not protect those drugs which are sensitive to light or air. Plastic boxes are impractical for inhalants, patches, salves or syrups.

In addition, a federal law is presently in place that requires that printed information regarding side effects and warnings, be provided to patients at the time of filling a prescription.

SUMMARY OF THE INVENTION

The invention provides a medication compliance system comprising an output device, and a computer communicating with the output device and having a computer program loaded therein to define a particular logic circuit which generates a graphical user interface with which a user indicates the number of times a particular pharmaceutical is to be taken during a day, and which causes the output device to print a label having data thereon identifying the pharmaceutical, and having a shape thereon representing the number of times a day the pharmaceutical is to be taken.

One aspect of the invention provides a system for producing visual aids to assist patients who take multiple medications. Both the timing of these medications and the number of medications taken in a day's time are addressed. In one embodiment, visual aids are prepared when a prescription is filled by a pharmacist, and is dispensed by the pharmacist.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. patent Laws "to promote the progress of science and useful arts" (Article 1, Section 8).

Figure 1:
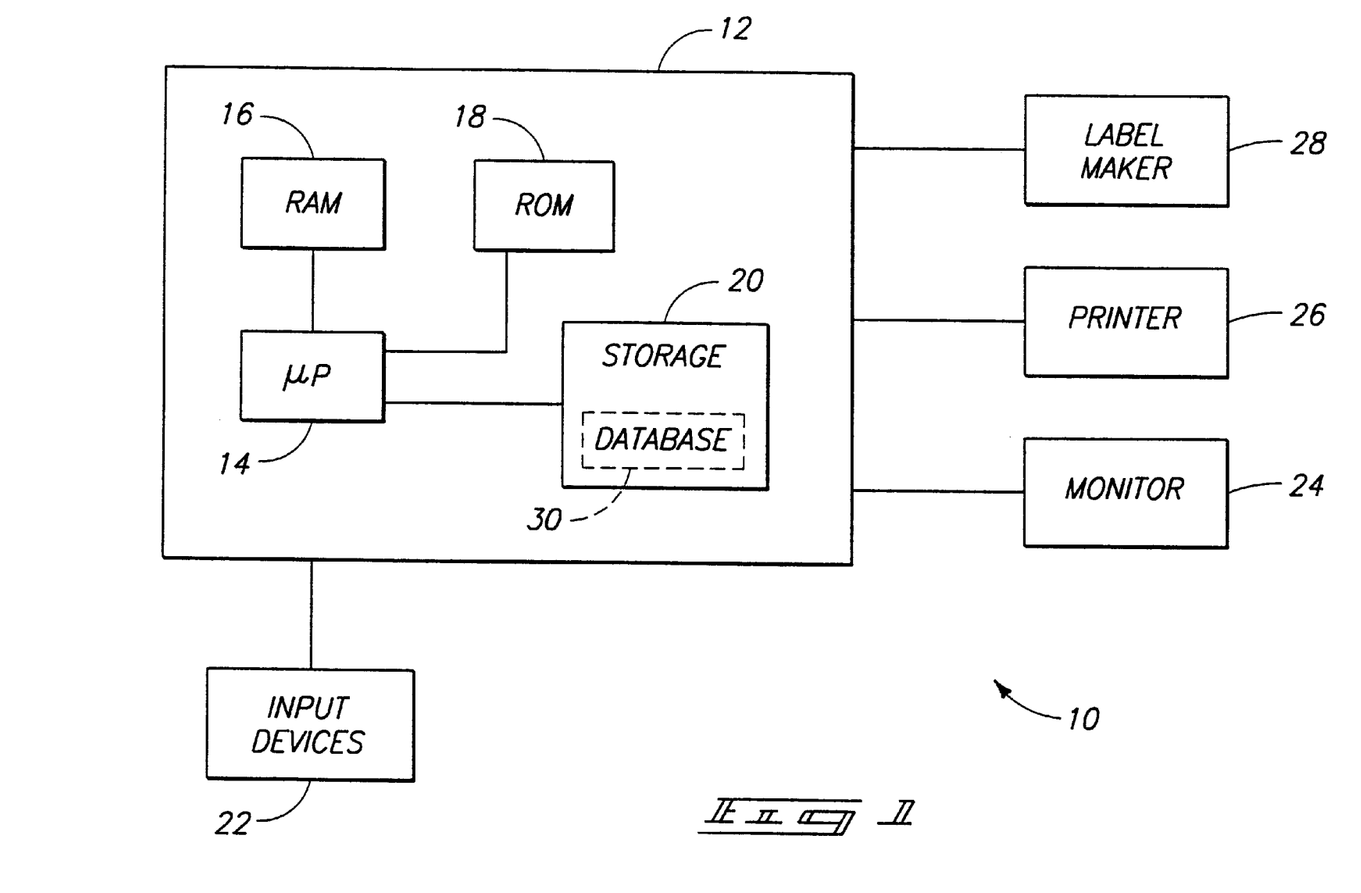
FIG. 1 is a block diagram illustrating a system embodying the invention.

FIG. 1 illustrates a system 10 embodying the invention. The system 10 comprises a computer 12, which can be a minicomputer, a microcomputer, a UNIX (TM) machine, a mainframe computer, a personal computer (PC) such as an Intel (TM) 286, 386, 486, Pentium (TM), or higher personal computer or clone thereof or Apple (TM), Macintosh (TM), or PowerPC (TM) personal computer or clone thereof, or any other appropriate computer. In one preferred embodiment, the computer 12 is a personal computer. The computer 12 includes typical components such as a microprocessor 14, RAM 16 in communication with the microprocessor 14, and ROM 18 in communication with the microprocessor 14, memory or storage 20 (e.g. hard drive, disk drive, tape unit, CD-ROM, etc.), serial ports (not shown), and parallel ports (not shown). The term "memory" is intended to encompass storage media such as hard drives, computer disks, backup tapes, optical disks, network drives, flash cards, CD-ROM disks, etc. as well to encompass hardware that read from and writes to the storage media. The system 10 further includes input devices 22 (e.g.; keyboard and mouse or touch screen) in communication with the computer 12, and output devices (e.g.; a monitor 24, a printer 26, and a label maker 28). In one embodiment, the printer 26 is used to print labels and the label maker 28 is omitted. The storage 20 includes a database 30 that will be described below in greater detail, as well as software for printing labels and charts as will be described below in greater detail.

Figure 2:
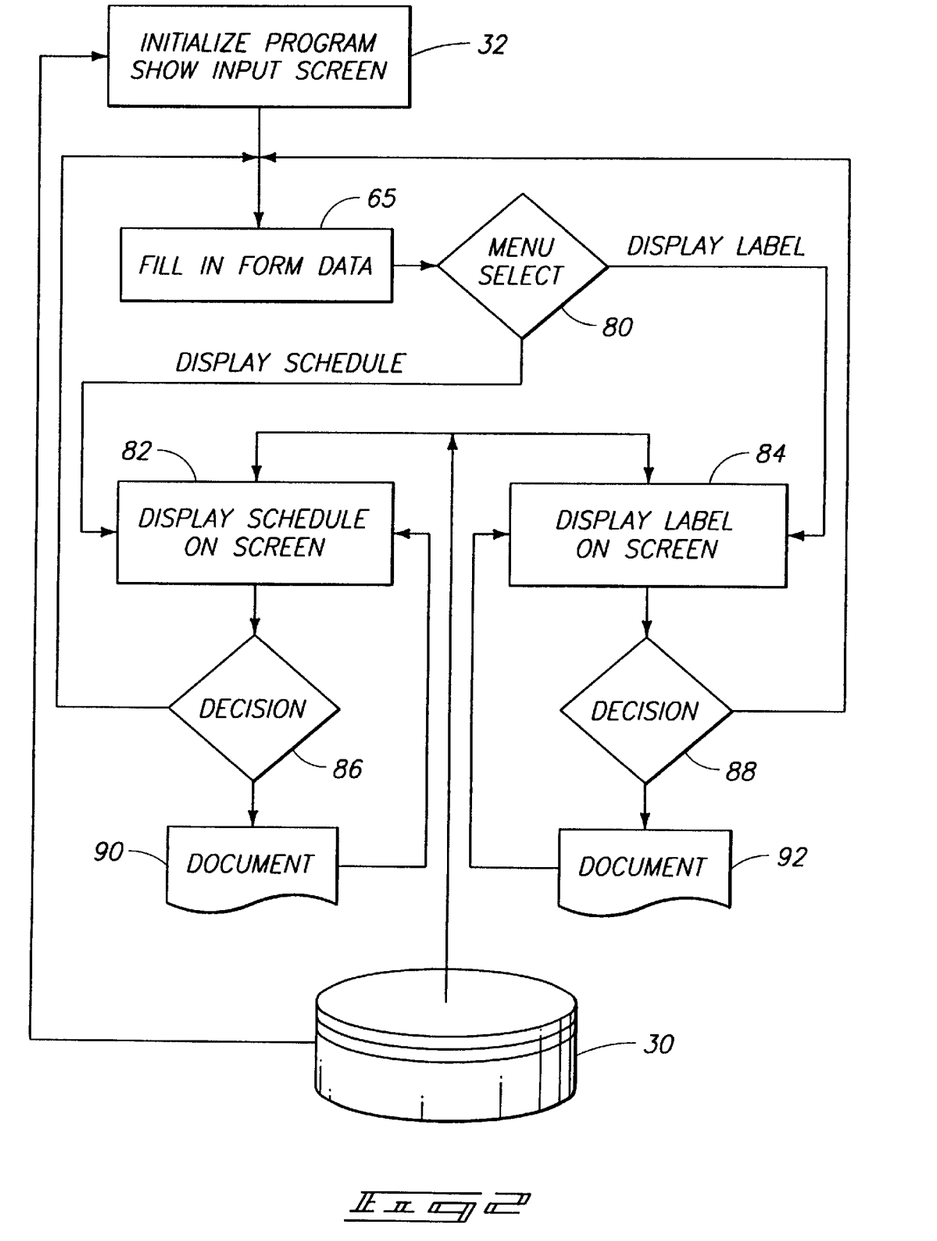
FIG. 2 is a flowchart for a software program implemented in the system of FIG. 1, in accordance with one embodiment of the invention, to define a specific digital logic circuit.
Figure 3:
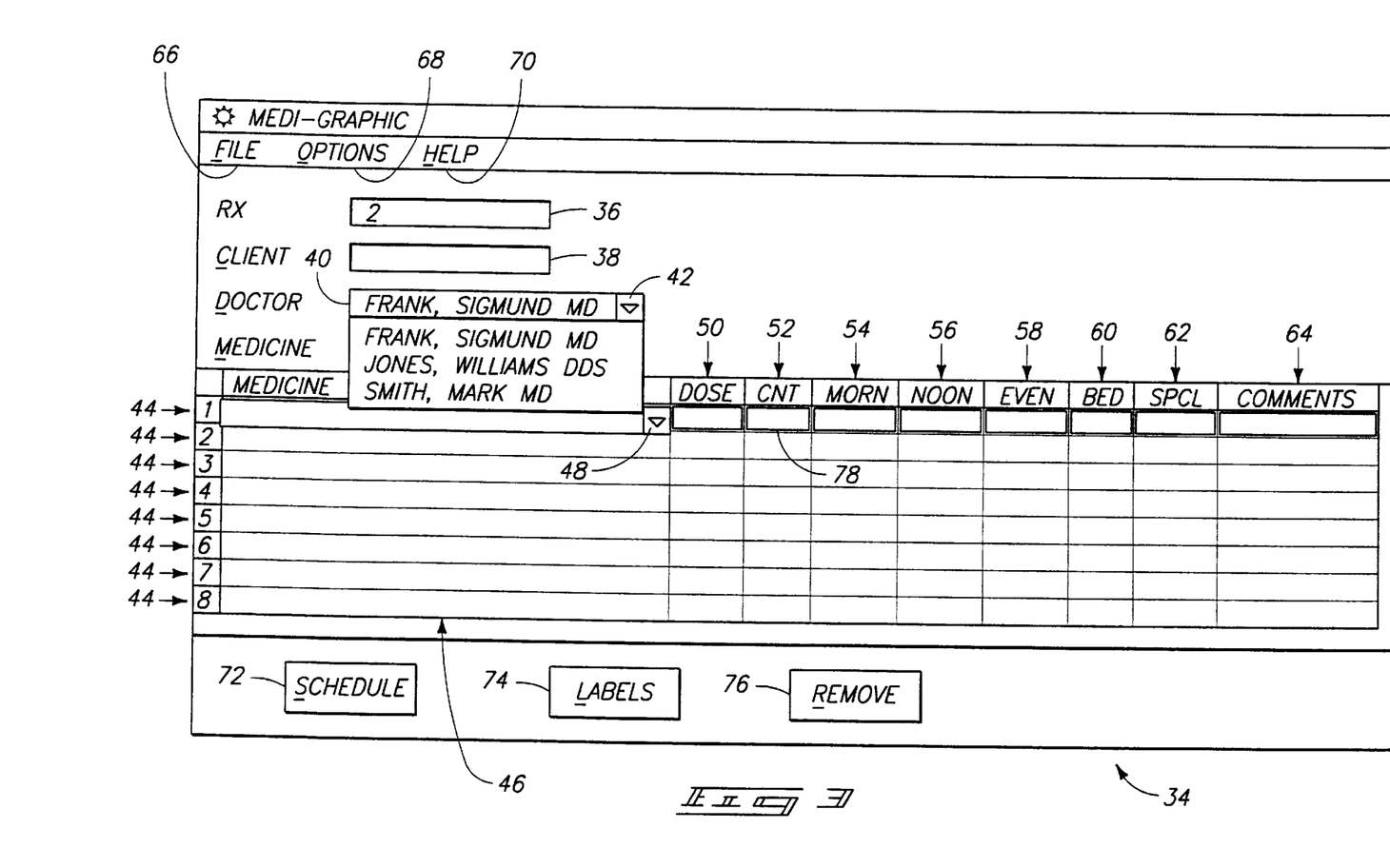
FIG. 3 illustrates a graphical user interface generated by the software of FIG. 2.

In step 32 (FIG. 2), the system provides a graphical user interface 34, such as the interface shown in FIG. 3, e.g., using the monitor 24. The interface provides a form which includes various fields which are filled in by a user, such as a pharmacist. The form interacts with the database 30, as described below.

The interface 34 includes a field 36 in which a prescription number is automatically entered. The number is incremented with each new prescription filled using the system. In one embodiment, the number increments without regard to whether the prescription is being filled for a repeat or new patient. In another embodiment, if a particular patient comes in with a new prescription, a different prescription number is used for that particular patient. The interface 34 further includes a field 38 in which data identifying the client (or patient) is filled in by the user. The data for field 38 is typically the name of the client, but can be other information such as a number (e.g., a patient number or social security number). The interface 34 further provides a field 40 in which the name of the client's doctor is entered.

In the illustrated embodiment, the field 40 is of a pull-down menu type, and includes a button 42 which, when pressed, causes a menu to appear. Names of many doctors are provided in the database 30, and the user can select a doctor by pushing or clicking on a pull down button 42, and by selecting a doctor from a list that appears (e.g., by clicking on the name of a desired doctor using the mouse, or by cursoring down to the name of the desired doctor and pressing enter using the keyboard). Thus, the user of the system does not need to memorize exact spellings of doctors names, and does not need to type in data in this field. In one embodiment, the database 30 is a Microsoft Access (TM) database. In one embodiment, the computer 12 can be reconfigured to use a different Access database to provide the list of doctors. For example to change the database used, a Windows initialization (.ini) file contained in a subdirectory containing the software is modified is modified as follows:

[Medigraf]
DocPath=c:\mydbdir\mydoctor.mdb
DocTable=TheDoctor
DocName=Name
DocIndex=Index.

This assumes that the software's name is Medigraf, that the user has a directory on the C drive of the computer 12 named mydbdir and on that directory there is a Microsoft Access database file named mydoctor.mdb. In that database there is a table named TheDoctor which contains two fields: Name and Index. The field called Name contains the names of the doctors, and the field named Index contains a long unique number for each row in the database.

The interface 34 further includes, in the illustrated embodiment, a plurality of rows 44. The rows 44 respectively include a field 46 in which a type of medicine is entered by the user. In the illustrated embodiment, the field 46 is of a pull-down menu type, and, when the row is selected, includes a button 48 which, when pressed, causes a menu to appear. Names of many types of pharmaceuticals are provided in the database 30, and the user can select a type of pharmaceutical by pushing or clicking on a pull down button 48, and by selecting a pharmaceutical from a list that appears (e.g., by clicking on the name of a desired pharmaceutical using the mouse, or by cursoring down to the name of the desired doctor and pressing enter using the keyboard). Thus, the user of the system does not need to memorize exact spellings of names of pharmaceuticals, and does not need to type in data in this field. After data for one row 44 is filled by the user, the user moves down to the second row, and the pull down menu button 48 moves down to the next row 44, so that the next pharmaceutical can also be selected using a pull down menu. The computer 12 can be reconfigured to use a different Access database to provide the list of pharmaceuticals.

The rows 44 respectively include a field 50 in which a dose is entered by the user for the pharmaceutical in the same row 44. The rows 44 further respectively include a field 52 in which a count is entered by the user for the pharmaceutical in the same row 44. The rows 44 further include fields 54, 56, 58, 60, and 62 in which the user designates when the pharmaceutical is to be taken. More particularly, in the illustrated embodiment, the interface 34 includes a field 54, which is to be selected if the pharmaceutical is to be taken in the morning, a field 56, which is to be selected if the pharmaceutical is to be taken at noon, a field 58, which is to be selected if the pharmaceutical is to be taken in the evening, a field 60 which is to be selected if the pharmaceutical is to be taken at bedtime, and a field 62 if the pharmaceutical is to be taken at a time that does not fall within the previously mentioned categories of fields 54, 56, 58, or 60, such as "when needed." In one embodiment, the user can click in a field 54, 56, 58, or 60 and the field will be filled with an option that changes with each click in the same field. For example, in one embodiment, by clicking once in a field 54, 56, 58, or 60, that field is filled with a "1." By clicking again in the same field, the "1" is changed to "1-2." By clicking again in the same field, the "1-2" is changed to a "2." Other options and sequences are possible, and different options may be presented for different fields. Each row 44 further includes a field 64 in which comments pertaining to the pharmaceutical in that row can be entered by the user.

The system 10 receives the filled form information from the user, for the various fields, in step 65 (FIG. 2).

Various alternative interfaces can be provided. For example, any of the fields of the interface 34 can be provided with pull-down menus. Further, organization can be by columns instead of by rows, or in other suitable manners.

The interface 34 further includes a pull down menu 66 labeled "File." By selecting the file menu 66, the user is provided with a menu option "exit" using which the user can exit the program. The interface 34 further includes a pull down menu 68 labeled "Options." By selecting the options menu 68, the user is provided with a menu of options using which the user can set the size of logos (e.g., height by width, or automatic based on the size of text) that will appear on labels described below, can set the file name of the business logo (e.g., the name of the pharmacy) that will appear on the labels, can select a printer (e.g., using a typical Windows printer selection interface), and can set the starting number for the field 36. The interface 34 further includes a pull down menu 70 labeled "Help." By selecting the help menu 70, the user is provided with a menu using which the user can find help in using the program, or can find information about the program (e.g., copyright notice, release date, version number, etc.).

The interface 34 further includes a button 72 which the user presses after filling in the various fields to cause the printer 26 to print a schedule based on the information filled in using the interface 34. More particularly, in the illustrated embodiment, after pushing the button 72, a representation of a schedule is displayed on the monitor 24 prior to printing to allow the user to see if it accurately reflects what the user intended. The user can then press a button to cause printing to begin. Examples of schedules are shown in FIGS. 7–10. The content of a schedule will vary depending on how the interface 34 is filled in.

Figure 4:
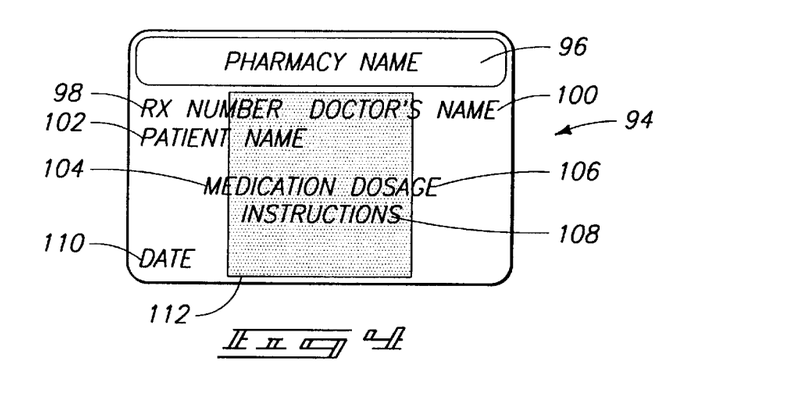
FIGS. 4–6 are plan views of examples of labels generated by the system when programmed using the software of FIG. 2.
Figure 5:
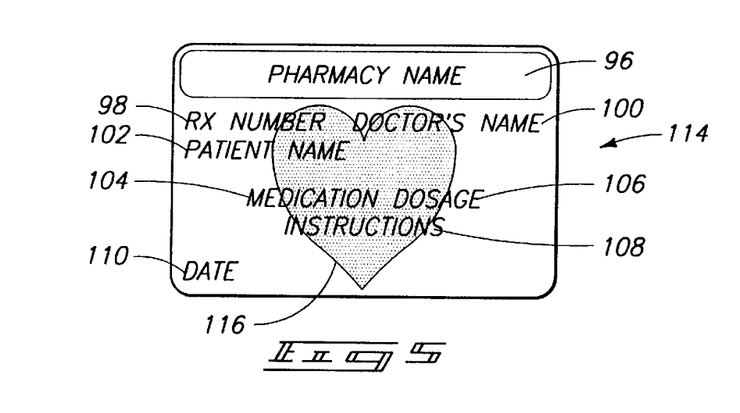
Figure 6:
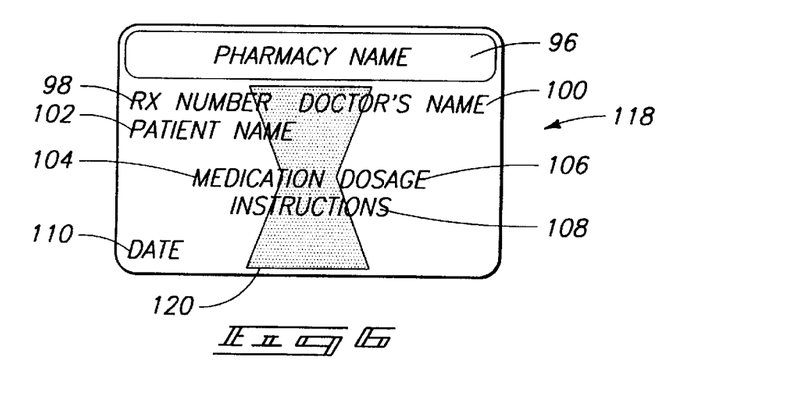

The interface 34 further includes a button 74 which the user presses after filling in the various fields to cause the printer 26 (or label maker 28) if the user desires to print a label (e.g., for pill containers) based on the information filled in a selected row 44 using the interface 34. More particularly, in the illustrated embodiment, after pushing the button 74, a representation of a label is displayed on the monitor 24 prior to printing to allow the user to see if it accurately reflects what the user intended. The user can then press a button to cause printing to begin. Examples of labels are shown in FIGS. 4–6. Labels for each row can be printed by selecting (highlighting) each row and pressing the button 74 while the row is selected.

The interface 34 further includes a button 76 using which the user can clear all data (e.g., data in fields 46, 50, 52, 54, 56, 58, 60, and 62) in whatever row 44 is selected. In FIG. 3, the first row is selected. This is indicated to the user, on the monitor 24, by bold boxes 78 around each field.

Pressing of a button 72 or 74 is indicated by step 80 in FIG. 2. If the button 72 is pressed, a schedule is displayed on the monitor 24, as indicated by step 82, making use of data from the database 30. After step 82 is performed, the user indicates in step 86 to the system 10 whether or not to print the schedule displayed on the monitor. If the user indicates to the system that the schedule is to be printed, the schedule is printed in step 90. If the user indicates to the system that the schedule is not to be printed, the system again displays the graphical user interface 34, allowing the user to change data in various fields.

If the button 74 is pressed, a label is displayed on the monitor 24, as indicated by step 84, making use of data from the database 30. After step 82 is performed, the user indicates in step 88 to the system 10 whether or not to print the label displayed on the monitor. If the user indicates to the system that the label is to be printed, the label is printed in step 92. If the user indicates to the system that the label is not to be printed, the system again displays the graphical user interface 34, allowing the user to change data in various fields.

A label 94 generated by the system 10 is shown in FIG. 4. The label 94 is intended to be placed on a pill dispenser (e.g., of the type including a housing in the shape of a hollow cylinder with a closed bottom and open top, and including a childproof cap). As such, the label 94 may include an adhesive backing of a type which is exposed by peeling away backing material or of a type that is activated by moisture.

The system causes the label 94 to be printed so as to include indicia or data 96 corresponding to the pharmacy name or logo. In the illustrated embodiment, the indicia is in the form of alphanumeric characters. This indicia is set using the options pull down menu 68 from the interface 34. More particularly, the user indicates to the system the location of a file containing the logo 96.

The system further causes the label 94 to be printed so as to include indicia or data 98 corresponding to the prescription number. In the illustrated embodiment, the indicia is in the form of alphanumeric characters. The prescription number indicia corresponds to the number showing in field 36 of the interface 34. For example, in an actual label, the information 98 might be something like: RX 313269.

The system further causes the label 94 to be printed so as to include indicia or data 100 corresponding to the name of the prescribing doctor. In the illustrated embodiment, the indicia is in the form of alphanumeric characters. The doctor name indicia is set using the field 40 in the interface 34. For example, in an actual label, the information 100 may be something like: DR. FRAZIER, MARK.

The system further causes the label 94 to be printed so as to include indicia or data 102 corresponding to the name of the patient. In the illustrated embodiment, the indicia is in the form of alphanumeric characters. The patient name information is set using the field 38 in the interface 34. For example, in an actual label, the information 102 may be something like: FOR: WHALEY, HUNT.

The system further causes the label 94 to be printed so as to include indicia or data 104 corresponding to the pharmaceutical in the pillbox to which the label 94 is affixed. In the illustrated embodiment, the indicia is in the form of alphanumeric characters. The pharmaceutical information is set using the field 46 in the interface 34. For example, in an actual label, the information 104 may be something like: ERYTHROMYCIN.

The system further causes the label 94 to be printed so as to include indicia or data 106 corresponding to the dosage which is to be taken by the client or patient. In the illustrated embodiment, the indicia is in the form of alphanumeric characters. The dosage information is set using the field 50 in the interface 34. For example, in an actual label, the information 106 may be something like: 500 MG. The information 106 may, in one embodiment, also include the count from the field 52 (e.g., the number of pills initially dispensed into the container).

The system further causes the label 94 to be printed so as to include indicia or data 108 corresponding to instructions given by the prescribing doctor. In the illustrated embodiment, the indicia is in the form of alphanumeric characters. The instructions are entered using the field 64 in the interface 34. For example, in an actual label, the information 108 may be something like: 1 OR 2 TABS EVERY 3–4 HRS AS NEEDED FOR PAIN.

The system further causes the label 94 to be printed so as to include indicia or data 110 corresponding to the date. The date is the system date of the computer using which the label is printed. For example, in an actual label, the information 110 may be something like: 1/20/97.

The system further causes the label 94 to be printed so as to include indicia or data 112 indicating how many times a day the pharmaceutical is to be taken. In the illustrated embodiment, the indicia comprises a geometric shape (or figure or design). More particularly, in the illustrated embodiment, the indicia is in the form of a watermark of a particular shape. The shape of the watermark depends on information contained in the corresponding row 44 of the interface 34. More particularly, in the illustrated embodiment, the watermark 112 is in the general shape of a square if the pharmaceutical associated with the label (and corresponding to the indicia 104 on the label) is to be taken four times a day, as calculated by the system. For example, if the row 44 for which the label was generated has a 1 in field 54, a 1 in field 56, a 1 in field 58, and a 1 in field 60, the system calculates that the pharmaceutical is to be taken four times a day, and the watermark printed on the label is in the shape of a square. In the illustrated embodiment, the shape of a square was selected to signify that a pharmaceutical is to be take four times because a square has four sides. In alternative embodiments, a diamond or other shape or indicia representative of the number four is printed on the label as a watermark or otherwise. However, if the row 44 for which the label was generated has a 2 in field 54, a 2 in field 60, and no entries or zeros in fields 56 and 58, the system calculates that the pharmaceutical is to be taken two times a day, and the watermark printed on the label is in the shape of an hourglass.

Indicia of different shapes, such as watermarks of different shapes, are printed depending on the information filled in using the interface 34. For example, FIG. 5 illustrates a label 114 having a watermark 116 in the shape of a heart. A watermark in the shape of a heart is generated by the system if a numerical entry is made in the field 62 instead of the fields 56, 56, 58, or 60. In alternative embodiments, another shape or indicia representative of a special category is printed on the label as a watermark or otherwise. The label 114 of FIG. 5 further includes indicia 96, 98, 100, 102, 104, 106, and 110 that varies depending on the information filled in using the interface 34, including information for a row 44 corresponding to the label, as described above in connection with the label 94.

In the illustrated embodiment, the shape of a heart was selected to signify that the pharmaceutical is to be taken on a special basis because a heart is a symbol representing love or special care.

FIG. 6 illustrates a label 118 having a watermark 120 in the general shape of an hourglass or superimposed opposing triangles. A watermark in this shape is generated by the system if numerical entries are made in exactly two of the fields 56, 56, 58, or 60. More particularly, in the illustrated embodiment, the watermark 112 is in the general shape of an hourglass if the pharmaceutical associated with the label (and corresponding to the indicia 104 on the label) is to be taken two times a day, as calculated by the system. In alternative embodiments, another shape or indicia representative of the number two is printed on the label as a watermark or otherwise. The label 114 of FIG. 5 further includes indicia 96, 98, 100, 102, 104, 106, and 110 that varies depending on the information filled in using the interface 34, including information for a row 44 corresponding to the label, as described above in connection with the label 94.

In the illustrated embodiment, the shape of an hourglass was selected to signify that the pharmaceutical is to be taken twice a day because an hourglass has two major portions.

Other shapes are generated by the system depending on the number of times a day the pharmaceutical for a row 44 is to be taken. For example, a watermark in the shape of a triangle is generated by the system if the pharmaceutical is to be taken three times a day. The shape of a triangle was selected because a triangle has three sides (and three angles). A watermark in the shape of a circle is generated by the system on the label for a row 44 if the pharmaceutical is to be taken once a day at noon (indicated by a 1 in field 56). The shape of a circle was selected because a circle corresponds to a noon sun. A watermark in the shape of a crescent moon is generated by the system on the label for a row 44 if the pharmaceutical is to be taken once a day at bedtime (indicated by a 1 in field 60). The shape of a crescent moon was selected because a moon represents late night. A watermark in the shape of an upwardly pointing arrow is generated by the system on the label for a row 44 if the pharmaceutical is to be taken once a day on rising (indicated by a 1 in field 54). The shape of an upwardly pointing arrow was selected because an upwardly directed arrow represents rising from bed. A watermark in the shape of a downwardly pointing arrow is generated by the system on the label for a row 44 if the pharmaceutical is to be taken once a day in the evening. The shape of a downwardly pointing arrow was selected because a downwardly directed arrow represents the end of a day.

Figure 11:
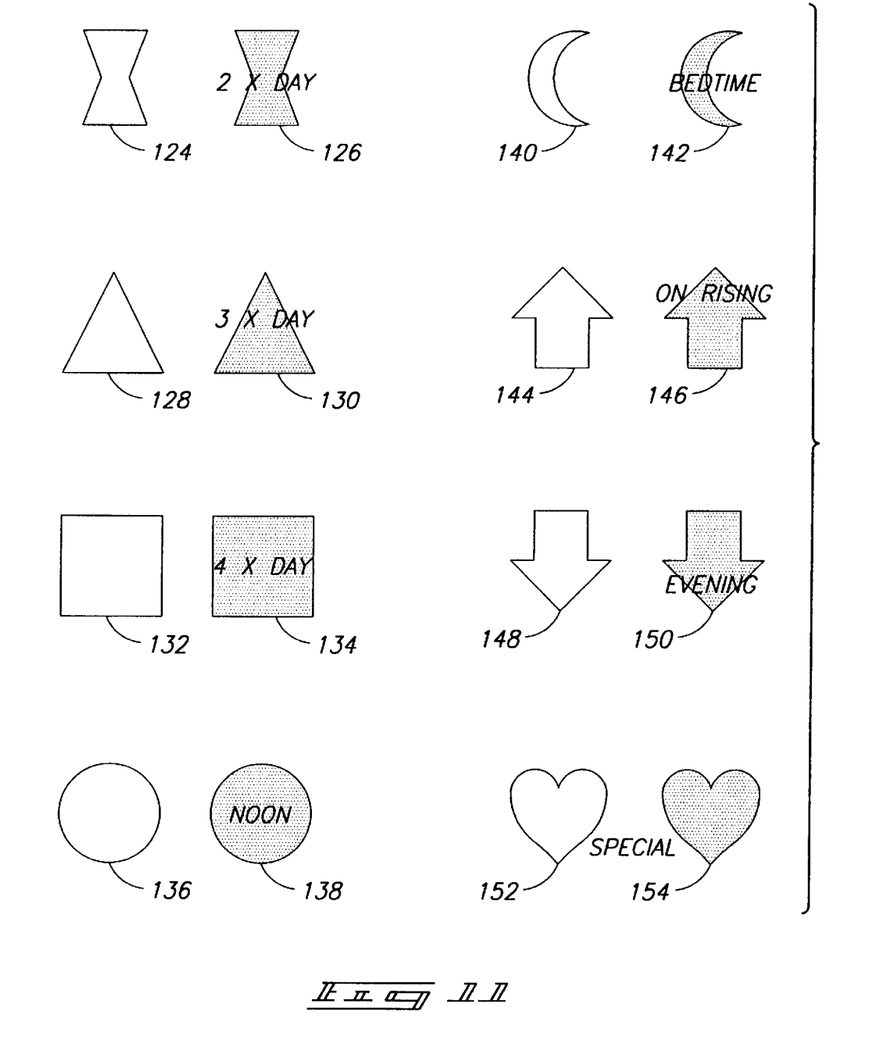
FIG. 11 is a plan view of an instructional sheet indicating meanings of symbols contained on charts and labels produced by the system.

These symbols are all shown in FIG. 11. More particularly, FIG. 11 represents an instruction sheet which can be given by pharmacists to patients to help explain the meanings of the various symbols which appear on the labels and schedules. FIG. 11 shows hourglass shapes 124 and 126 along with text "2×day" signifying that the hourglass symbol indicates that a pharmaceutical is to be taken two times a day, triangles 128 and 130 along with text "3×day" signifying that the triangle symbol indicates that a pharmaceutical is to be taken three times a day, squares 132 and 132 along with text "4×day" signifying that the square symbol indicates that a pharmaceutical is to be taken four times a day, circles 136 and 138 along with text "noon" signifying that the circle symbol indicates that a pharmaceutical is to be taken at noon, crescent shapes 140 and 142 signifying that the crescent symbol indicates that a pharmaceutical is to be taken at bedtime, upwardly directed arrows 144 and 146 along with text "on rising" signifying that the upwardly directed arrow symbol indicates that a pharmaceutical is to be taken on rising, downwardly directed arrows 148 and 150 along with text "evening" signifying that the downwardly directed arrow symbol indicates that a pharmaceutical is to be taken in the evening, and hearts 152 and 154 along with text "special category" signifying that the heart symbol indicates that a pharmaceutical is to be taken at special times (e.g., as needed, or more than four times a day).

The shapes 124, 128, 132, 136, 140, 144, 148, and 152 shown in FIG. 11 are hollow, while shapes 126, 130, 134, 138, 142, 146, 150, and 154 are solid. Hollow shapes, in the labels and schedules, indicate optional conditions. For example, a hollow shape shadows a solid one if medication instructions inputted using the graphical user interface indicate "one or two . . . " to be taken as determined by the patient. If a particular pharmaceutical is to be taken one to two times a day, as indicated by a "1-2" in one of the fields 54, 56, 58, and 60, the shape employed will be the shape for one time a day, but there will be one solid shape and one hollow shape. Thus, the shape employed in the schedules and labels will be the shape corresponding to the number of fields 54, 56, 58, and 60 for which non-zero entries were made using the graphical user interface, including one hollow shape if an alternative (e.g. "1-2") is presented in any of the fields 54, 56, 58, and 60. The hollow shape will appear in the field corresponding to the field in the graphical user interface where the alternative (e.g. "1-2") was entered.

Other shapes that convey similar meanings can be employed in alternative embodiments. Further, indicia of other than shapes can be employed. This indicia does not necessarily need to be in the form of a watermark.

Figure 7:
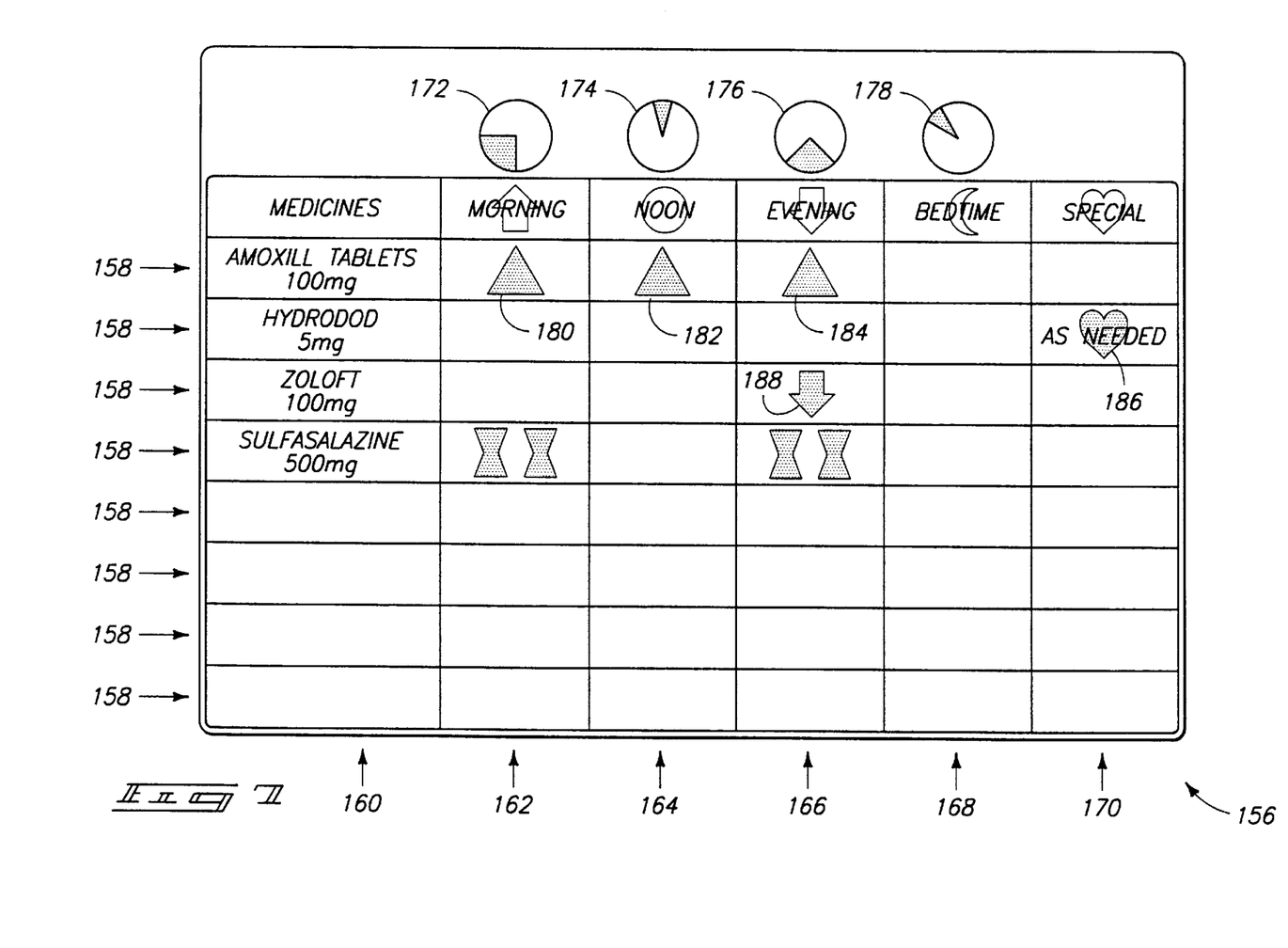
FIGS. 7–10 are plan views of examples of charts generated by the system when programmed using the software of FIG. 2.
Figure 8:
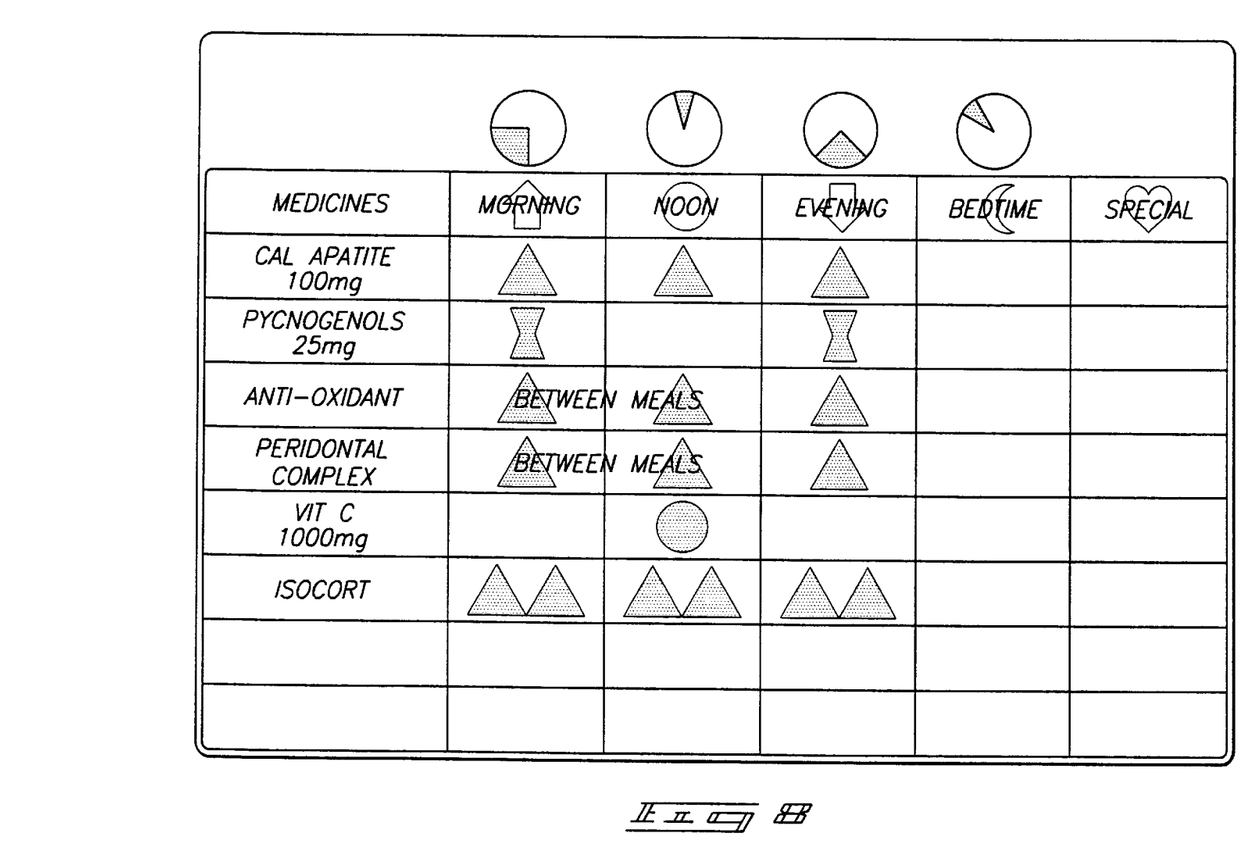
Figure 9:
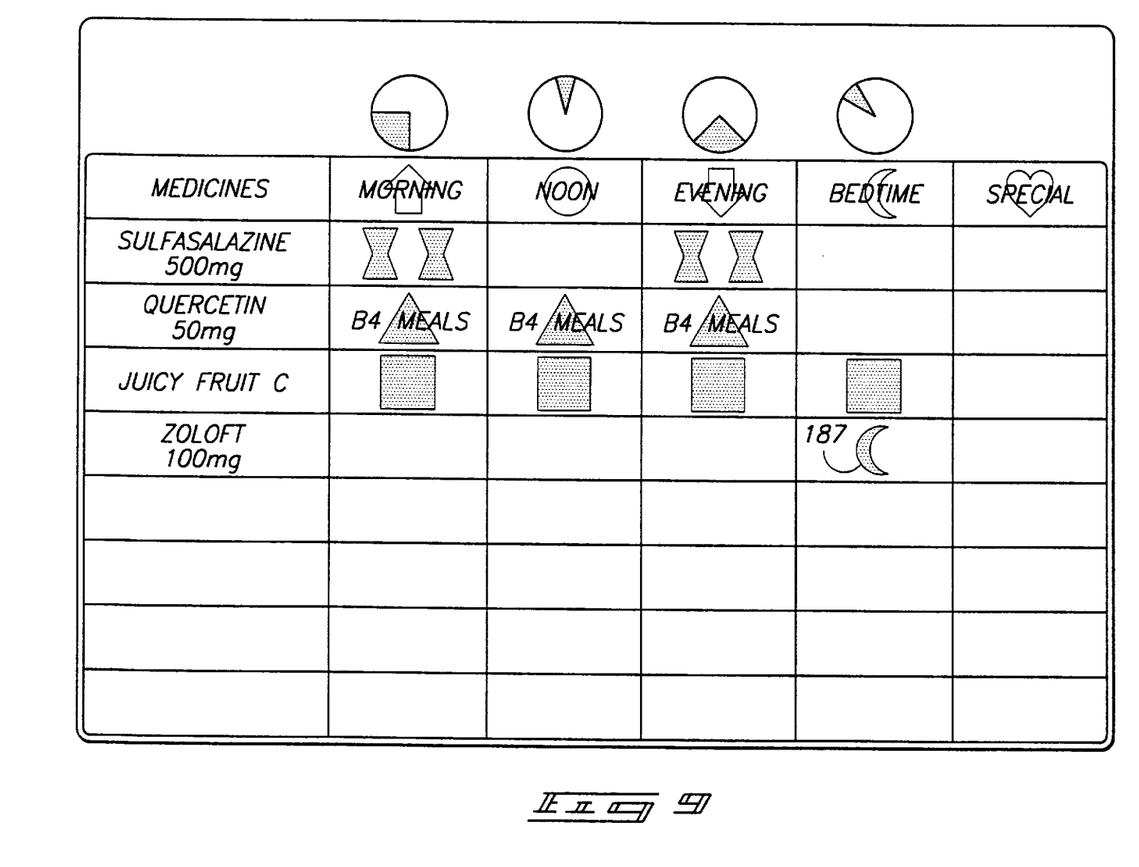
Figure 10:
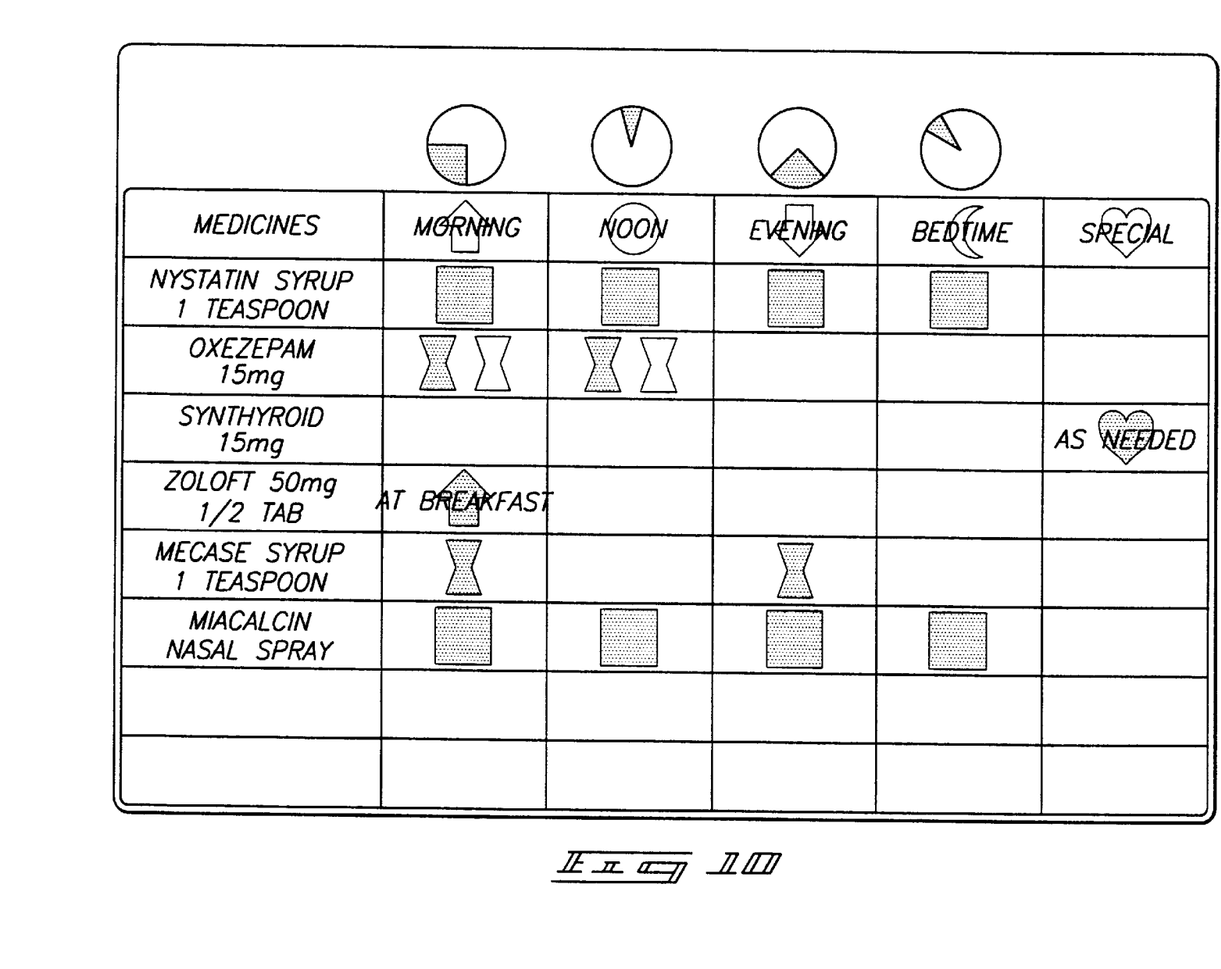

A schedule 156 generated or printed by the system 10 is shown in FIG. 7. The schedule 156 is given to the patient along with pillboxes bearing the above described labels. While each label corresponds to one of the rows 44 of the graphical user interface 34, the schedule 156 includes information relating to all of the rows 44 of the graphical user interface 34. The schedule is intended to provide comprehensive information about multiple pharmaceuticals taken by the patient in a simple to understand format.

The schedule 156 includes rows 158 corresponding to the rows 44 of the graphical user interface 34. In the illustrated embodiment, the number of rows 158 is equal to the number of rows 44. The information included in the rows 158 is derived from information placed in respective rows 44. The respective rows 158 include a field or area 160 in which indicia corresponding to the name of the pharmaceutical indicated in the field 46 of the corresponding row 44 of the interface 34. For example, if "Amoxill tablets" was input in field 46 of the first row 44 of the interface 34, the words Amoxill tablets will appear in field 160 of the first row 158 of the schedule 156. The field 160 further includes dosage information corresponding to information indicated in the field 50 of the corresponding row 44 of the interface 34.

The schedule 156 further includes fields 160, 162, 164, 166, 168, and 170, for each row 158, corresponding to the fields 54, 56, 58, 60, and 62, respectively, of the interface 34. Above the fields 162, 164, 166, and 168 are symbols 172, 174, 176, and 178, respectively, having shapes representing clocks with areas shaded to represent the time of day associated with the field. The schedule 156 further includes geometric shapes in the fields 162, 164, 166, 168, and 170 which vary depending on the information input using the interface 34 in a manner similar to the manner in which geometric shapes are selected for the labels. More particularly, if a pharmaceutical for a row 44 is to be taken three times a day, a triangular shape is placed in selected fields 162, 164, 166, or 168 depending on what was entered in the graphical user interface 34. For example, if a "1" was entered in field 54, a "1" was entered in field 56, and a "1" was entered in field 58, but field 60 is left blank or a "0" is entered in field 60, for the first row 44, triangles 180, 182, and 184 will appear in fields 162, 164, and 166, respectively, for the first row 158. If a "1" is entered in field 62 of the second row 44 of the interface, but fields 54, 56, 58, and 60 are left blank (or "0" is entered), then a heart 186 will appear in field 170 for the second row 158 of the schedule. Whatever comments are entered in field 64 for the row 44 appear over the shape or symbol. Thus, if "AS NEEDED" was entered in field 64 of the second row 44, "AS NEEDED" will appear across the heart 186 in the second row 158 of the schedule. A single entry of "1" in field 60 of a row 44 of the interface will cause a crescent moon 187 in field 168 for the corresponding row 158 of the schedule. A single entry of "1" in field 58 of a row 44 of the interface will cause a down arrow 188 in field 166 for the corresponding row 158 of the schedule.

Thus the shape appearing in fields 162, 164, 166, and 168 depends on the number of fields in the collection 54, 56, 58, and 60 that have non-zero entries. The location of the shape depends on the location of the entries in the same collection of fields and the number of shapes in each location 162, 164, 166, and 168 depends on the data in the corresponding field 54, 56, 58, and 60, respectively. If the data in a field 54, 56, 58, or 60 is "1", there will be one solid shape in field 162, 164, 166, or 168, respectively. If the data in a field 54, 56, 58, or 60 is "1-2", there will be one solid shape and one hollow shape in the corresponding field 162, 164, 166, or 168, respectively. If the data in a field 54, 56, 58, or 60 is "2", there will be two solid shapes in the corresponding field 162, 164, 166, or 168, respectively.

Various alternative schedules will be generated by the system depending on information entered in the graphical user interface for a patient. Hollow symbols or shapes in the schedule represent optional behavior by the patient, as described above.

The invention assists those who fill prescriptions in meeting the requirements of the above-mentioned federal law.

The invention provides a medication compliance tool as well as a risk management aid. One aspect of the invention provides a system for creating a label for a medication container or pillbox, such as a container of the type used to hold prescription medicines.

The shape appears as a "watermark" behind the pertinent text on the bottle label, and is then depicted on the chart, situated below the times of day for medication. In one embodiment, all the text, both on the labels and on the chart, are sans-serif, bold and easy to read. The shapes have inherent meaning, i.e., they indicate the number of times a day or a particular time of day. A hollow shape shadows the solid one if the medication instructions indicate "one or two . . . " to be taken as determined by the patient.

Another aspect of the invention provides a chart that is coded to the bottle label by shape. The chart has space for up to and including eight medications. Any patient taking more than eight medications receives a second chart page print-out. A third page may be generated, if the number of medications exceeds sixteen, etc.

This system, which generates the above mentioned visual aids, is designed to reduce the possibility of the patient taking medications at the wrong time or in the wrong quantity. In one aspect of the invention, a letter-size handout describing the shapes and their significance is provided to a patient at the time of first purchase. After a patient is acquainted with the shapes and their meanings, they are able to manage the medications with greater ease. If the patient loses or damages the chart, the patient will still have the watermark on the pill container to remind them of how often they should be taking it. Medications that are to be taken multiple-times throughout a day are easily differentiated from medications to be taken "once-a-day." A replacement chart can be prepared by the pharmacist who filled the prescription, upon request, because this pharmacist will have the patient "file" in the computer. The visual aids produced by the system can also be used effectively by people who know another language, as the visual aids are pictogram-based.

This computer-generated visual system is more reliable than a manual system of medication management due to the accuracy of the initial input. At each re-issuance of a prescription, changes are instantly made on the computer, and the labels and the chart match accordingly. Modifications, if necessary, are established with each refill.

The chart also has the capacity to carry pertinent information regarding any particular drug. For instance, phrases like "with food," "on empty stomach" or "no alcohol" can be entered by the pharmacist at the time of bottle label preparation. These information phrases appear on top of the particular shape designation on the chart. This is more visible than the tiny stick-on labels with microscopic text that are currently being used on medication bottles.

In one embodiment, the providers of pharmaceutical software to the pharmacy industry merge the software provided in accordance with one aspect of the invention into their existing system. The software then becomes part of the sequence of their software program, which includes a database of all available drugs, insurance companies and inventory, as well as local physicians and patients. The money saved across the entire health care system by avoiding major hospitalizations and encouraging correct medical treatment, is massive. A subtle outcome is that independence is restored for those cognizant elderly and chronically ill who previously needed help from others to properly take medications beforehand. In the caretaker setting, this visual system saves time and assures accurate medicating. Nursing professionals will also experience the same efficacy in patient care.

The system of the preferred embodiment is designed to help the elderly, the chronically ill, organ-transplant patients, AIDS patients toward the end of their treatment, people on kidney dialysis, patients receiving chemotherapy and radiation, as well as anyone on multiple medications. In addition, it assists care givers and nursing professionals in the proper use and management of multiple medications.

In the illustrated embodiment, the system includes software which is a Windows™-based program that can be used on a standard Personal Computer. This software program can easily be merged into existing software applications operating on large networked systems. With the architecture of computer platforms becoming increasingly open, this merging of additional programming into the existing structure grows more simple to execute.

These symbols are destined to become universal communicators, thus making the implementation of this system of global significance. A retiree would be able to refill their prescriptions abroad while traveling. Language barriers are not an issue in using this medication compliance tool. The intuitiveness of the design succeeds in its simplicity and elegance, and provides enormous assistance to the person needing to take multiple medications precisely.

In compliance with the patent statutes, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A medication compliance system comprising:
  an output device; and
  a computer communicating with the output device and having a computer program loaded therein to define a particular logic circuit which generates a graphical user interface with which a user indicates the number of times a particular pharmaceutical is to be taken during a day, and which causes the output device to print a label having data thereon identifying the pharmaceutical, and having a shape thereon, the shape being selected in response to the number of times, indicated by the user with the graphical user interface, that the pharmaceutical is to be taken, and wherein a shape may be duplicated for different pharmaceuticals.

2. A medication compliance system in accordance with claim 1 wherein the output device is a printer.

3. A medication compliance system in accordance with claim 1 wherein the generated shape is in the form of a watermark.

4. A medication compliance system in accordance with claim 3 wherein the watermark is a square if the user indicated that the pharmaceutical is to be taken four times a day.

5. A medication compliance system in accordance with claim 3 wherein the watermark is a triangle if the user indicated that the pharmaceutical is to be taken three times a day.

6. A medication compliance system in accordance with claim 3 wherein the watermark has the general appearance of an hourglass if the user indicated that the pharmaceutical is to be taken two times a day.

7. A program storage device readable by a machine, tangibly embodying a program of instructions executable by the machine to perform a method comprising:
  generating a graphical user interface having a plurality of fields in which names of pharmaceuticals can be entered, and having a plurality of fields associated with respective entered pharmaceuticals, the fields associated with respective pharmaceuticals including fields representing different times of a day when the pharmaceutical is to be taken, the graphical user interface accepting data representative of a number in respective fields representing different times of the day;
  calculating the number of times a day respective pharmaceuticals are to be taken by adding the numbers of fields representing different times of the day for a particular pharmaceutical that have non-zero entries;
  selectively generating a chart including a plurality of fields in which pharmaceuticals are listed, corresponding to the pharmaceuticals selected by the user using the graphical user interface, and including a plurality of fields associated with each pharmaceutical including fields representing different times of the day, and placing in these fields representing different times of the day shapes selected depending on the calculated number of times a day the pharmaceutical associated with the fields is to be taken; and
  selectively generating a label by a printer coupled to the machine, the label having data thereon identifying one of the pharmaceuticals entered using the graphical user interface, and having a shape thereon representing the calculated number of times a day the pharmaceutical is to be taken.

8. A system in accordance with claim 7 wherein at least one of the fields in which the names of pharmaceuticals can be entered includes a pop up menu including a list of names of pharmaceuticals.

9. A system in accordance with claim 8 and further comprising a user alterable database containing the list of names of pharmaceuticals.

10. A system in accordance with claim 7 wherein the graphical user interface further includes a field in which the name of a doctor can be entered, which field includes a pop up menu including a list of names of doctors.

11. A system in accordance with claim 8 and further comprising a user alterable database containing the list of names of pharmaceuticals.

12. A system in accordance with claim 7 wherein the shape on the label is in the form of a watermark.

13. A system in accordance with claim 12 wherein the shape of the watermark is a square if the user indicated that the pharmaceutical is to be taken four times a day.

14. A system in accordance with claim 12 wherein the shape of the watermark is a triangle if the user indicated that the pharmaceutical is to be taken three times a day.

15. A system in accordance with claim 12 wherein the shape of the watermark has the general appearance of an hourglass if the user indicated that the pharmaceutical is to be taken two times a day.

16. A system in accordance with claim 12 wherein the graphical user interface includes a field in which a user can indicate that a pharmaceutical is to be taken at noon, and wherein the shape of the watermark has the general appearance of a circle if the user indicated that the pharmaceutical is to be taken at noon.

17. A system in accordance with claim 12 wherein the graphical user interface includes a field in which a user can indicate that a pharmaceutical is to be taken at bedtime, and wherein the shape of the watermark has the general appearance of a crescent if the user indicated that the pharmaceutical is to be taken at bedtime.

18. A system in accordance with claim 12 wherein the graphical user interface includes a field in which a user can indicate that a pharmaceutical is to be taken on rising, and wherein the shape of the watermark has the general appearance of an upwardly directed arrow if the user indicated that the pharmaceutical is to be taken on rising.

19. A system in accordance with claim 12 wherein the graphical user interface includes a field in which a user can indicate that a pharmaceutical is to be taken during the evening, and wherein the shape of the watermark has the general appearance of a downwardly directed arrow if the user indicated that the pharmaceutical is to be taken in the evening.

20. A program storage device readable by a machine, tangibly embodying a program of instructions executable by the machine to perform a method comprising:

generating a graphical user interface having a plurality of fields in which names of pharmaceuticals can be entered, and having a plurality of fields associated with respective entered pharmaceuticals, the fields associated with respective pharmaceuticals including fields representing different times of a day when the pharmaceutical is to be taken, the graphical user interface accepting data representative of a number in respective fields representing different times of the day;

calculating the number of times a day respective pharmaceuticals are to be taken;

selectively generating a chart including a plurality of fields in which pharmaceuticals are listed, corresponding to the pharmaceuticals selected by the user using the graphical user interface, and including a plurality of fields associated with each pharmaceutical including fields representing different times of the day, and placing in these fields representing different times of the day shapes selected depending on the calculated number of times a day the pharmaceutical associated with the fields is to be taken; and selectively generating a label by a printer coupled to the machine, the label having data thereon identifying one of the pharmaceuticals entered using the graphical user interface, and having a watermark thereon in a shape representing the calculated number of times a day the pharmaceutical is to be taken, wherein the shape of the watermark is a square if the user indicated that the pharmaceutical is to be taken four times a day, wherein the shape of the watermark is a triangle if the user indicated that the pharmaceutical is to be taken three times a day, wherein the shape of the watermark has the general appearance of an hourglass if the user indicated that the pharmaceutical is to be taken two times a day, and wherein, if the pharmaceutical is to be taken one time a day, the shape of the watermark is selected based on when during the day the pharmaceutical is to be taken.

21. A program storage device readable by a machine, tangibly embodying a program of instructions executable by the machine to perform a method comprising:

generating a graphical user interface having a plurality of fields in which names of pharmaceuticals can be entered, and having a plurality of fields associated with respective entered pharmaceuticals, the fields associated with respective pharmaceuticals including fields representing different times of a day when the pharmaceutical is to be taken, the graphical user interface accepting data representative of a number in respective fields representing different times of the day;

calculating the number of times a day respective pharmaceuticals are to be taken by adding the numbers of fields representing different times of the day for a particular pharmaceutical that have non-zero entries;

generating a chart including a plurality of fields in which pharmaceuticals are listed, corresponding to the pharmaceuticals selected by the user using the graphical user interface, and including a plurality of fields associated with each pharmaceutical including fields representing different times of the day, and placing in these fields representing different times of the day shapes selected depending on the calculated number of times a day the pharmaceutical associated with the fields is to be taken; and generating a label by a printer coupled to the machine, the label having data identifying one of the pharmaceuticals entered using the graphical user interface, and having a shape representing the calculated number of times a day the pharmaceutical is to be taken.

22. A medication compliance system comprising:

an output device; and a computer communicating with the output device and having a computer program loaded therein to:

generate a graphical user interface having a plurality of fields in which names of pharmaceuticals can be entered, and having a plurality of fields associated with respective entered pharmaceuticals, the fields associated with respective pharmaceuticals including fields representing different times of a day when the pharmaceutical is to be taken, the graphical user interface accepting data representative of a number in respective fields representing different times of the day;

calculate the number of times a day respective pharmaceuticals are to be taken by adding the numbers of fields representing different times of the day for a particular pharmaceutical that have non-zero entries;

generate a printable file having data identifying one of the pharmaceuticals entered using the graphical user interface, and having a printable shape thereon representing the calculated number of times a day the pharmaceutical is to be taken, and cause the output device to print a label identifying the one of the pharmaceutical and the printable shape representing the calculated number of times a day the pharmaceutical is to be taken using the printable file.

* * * * *